(12) United States Patent
Li et al.

(10) Patent No.: US 8,334,426 B1
(45) Date of Patent: Dec. 18, 2012

(54) METHOD FOR OBTAINING TRANSFORMED MAIZE PLANTS

(75) Inventors: Yinghong Li, Urbandale, IA (US); Jijun Zou, Johnston, IA (US); Igor C. Oliveira, Johnston, IA (US)

(73) Assignee: Pioneer Hi Bred International Inc, Johnston, IA (US)

( * ) Notice: Subject to any disclaimer, the term of this patent is extended or adjusted under 35 U.S.C. 154(b) by 0 days.

(21) Appl. No.: 12/478,008

(22) Filed: Jun. 4, 2009

(51) Int. Cl.
*C12N 15/82* (2006.01)

(52) U.S. Cl. ........ 800/278; 800/295; 435/410; 435/412; 435/419; 435/430; 435/430.1

(58) Field of Classification Search .................. 800/278, 800/295; 435/410, 412, 419, 430, 430.1
See application file for complete search history.

(56) References Cited

U.S. PATENT DOCUMENTS

| | | | |
|---|---|---|---|
| 5,631,152 A | 5/1997 | Fry et al. | |
| 6,235,529 B1 * | 5/2001 | Lemaux et al. | 435/430.1 |
| 6,603,061 B1 | 8/2003 | Armstrong et al. | |
| 6,822,144 B1 | 11/2004 | Zhao et al. | |
| 6,995,016 B2 * | 2/2006 | Eudes et al. | 435/430.1 |
| 7,057,089 B2 * | 6/2006 | Ranch et al. | 800/293 |
| 7,238,862 B2 | 7/2007 | Allison et al. | |
| 2002/0120961 A1 | 8/2002 | Ranch et al. | |
| 2005/0183160 A1 * | 8/2005 | Burns et al. | 800/278 |

OTHER PUBLICATIONS

Lee et al. "Recovery of Transgenic Events from Two Highly Recalcitrant Maize (*Zea mays* L.) Genotypes using Agrobacterium-mediated standard-binary-vector Transformation," Maydica 52 (2007): 457-469.*
Schulze, J. "Improvements in Cereal Tissue Culture by Thidiazuron: A Review," Fruit, Vegetable and Cereal Science and Biotechnology; 1(2), 64-79, 2007, Global Science Books.*

* cited by examiner

*Primary Examiner* — Susan McCormick Ewoldt
(74) *Attorney, Agent, or Firm* — Pioneer Hi-Bred Int'l., Inc.

(57) ABSTRACT

Methods are provided for transforming isolated, immature maize embryos and for producing transgenic maize plants. The methods additionally comprise identifying or selecting transformed cells and regenerating such cells into transformed maize plants.

12 Claims, 1 Drawing Sheet

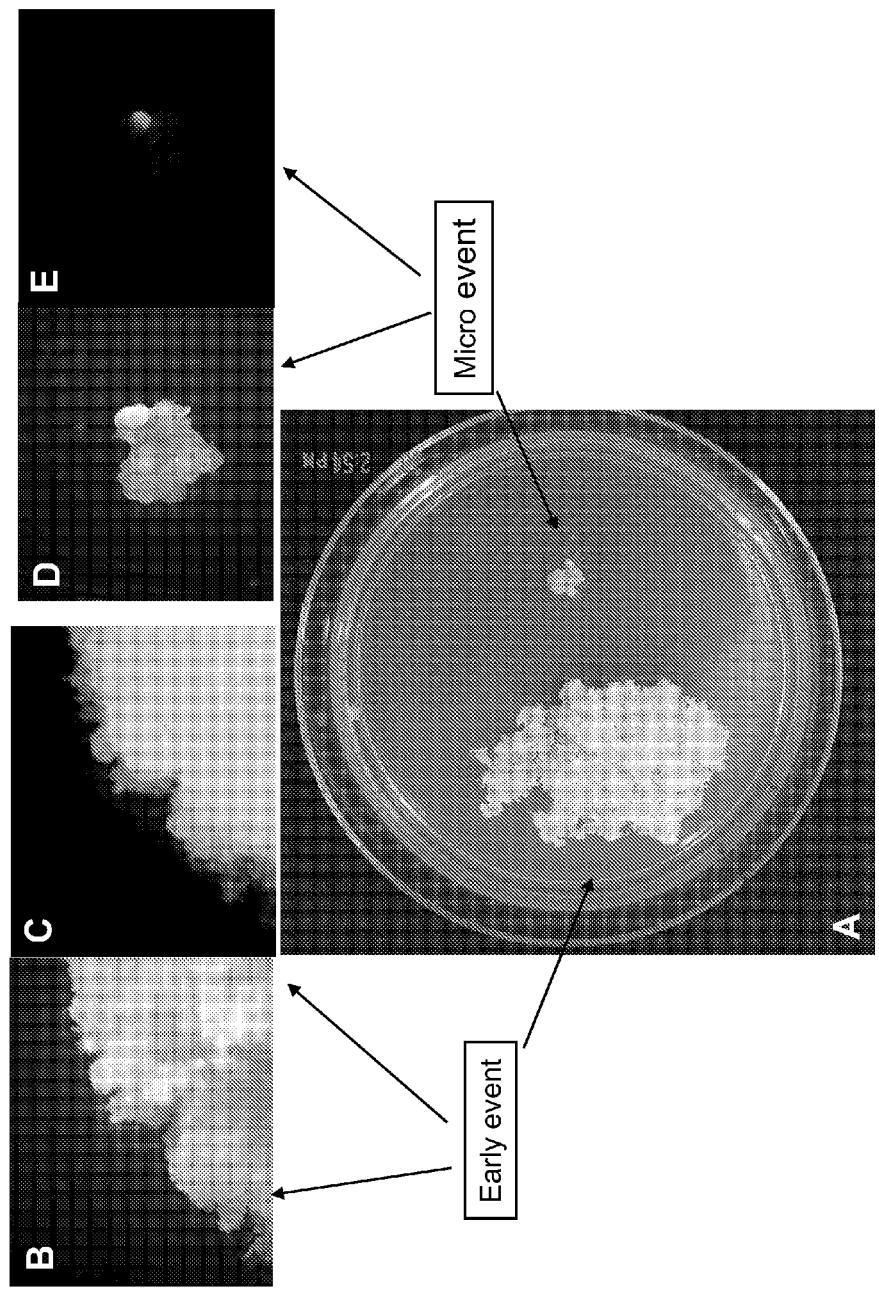

METHOD FOR OBTAINING TRANSFORMED MAIZE PLANTS

FIELD OF THE INVENTION

The present invention relates to the field of genetic engineering. The invention further relates to transforming plant cells and regenerating transformed plants from transformed plant cells.

BACKGROUND

The development of methods for the introduction of foreign genes into organisms has had a profound impact on the field of agriculture. While the movement of genes within plant species or between closely related plant species by traditional methods based on sexual reproduction has played an important role in crop improvement for most of this century, the pace of crop improvement by such methods has been slow and limiting due to the reliance on naturally occurring genes. The development of genetic transformation methods allows the introduction of recombinant DNA, into organisms. The recombinant DNA methods which have been developed have greatly extended the sources from which genetic information can be obtained for crop improvement. New crop plant varieties, developed through recombinant DNA methods, have reached the marketplace. Genetically engineered soybeans, maize, canola and cotton are now widely utilized by North America farmers.

Rapid progress has been made in developing the tools for manipulating genetic information in plants. Plant genes are being cloned, genetic regulatory signals deciphered, and genes transferred from entirely unrelated organisms to confer new agriculturally useful traits to crop plants. Recombinant DNA methods significantly increase the gene pool available for crop improvement. While the genetic sources for sequences for crop improvement have greatly expanded, the number of genotypes which can by stably transformed to recover a fertile plant are still limited. Therefore, methods which expand the scope of target recipient genotypes and/or improve recovery of fertile transformed plants from these genotypes are needed.

SUMMARY

Methods are provided for transforming immature maize embryos and for producing transgenic maize plants. The methods can be used for the incorporation of new traits into cultivated maize plants. The methods comprise obtaining immature embryos from a maize plant and introducing a nucleotide construct into cells from the immature embryos and regenerating plants from somatic embryos that do not result from a proembryogenic mass of cells. The methods additionally comprise identifying or selecting transformed cells and regenerating such cells into transformed maize plants. Also provided are methods that involve the introduction of a nucleotide construct into cells from an immature embryo by *Agrobacterium* or particle bombardment. Such methods are particularly directed to the introduction of a nucleotide construct into cells of an isolated, immature embryo.

BRIEF DESCRIPTION OF THE DRAWINGS

FIG. 1: An exemplary comparison of an early Type II callus event and a micro event is shown. Panel A is a light micrograph of the two events on the same media plate. Panels B and C are close-up micrographs of the early event photographed with visible light, and a fluorescent filter respectively. Panels D and E are close-up micrographs of the micro event photographed with visible light, and a fluorescent filter respectively.

DETAILED DESCRIPTION

Improved methods for transforming maize cells and regenerating transformed maize plants are desired. The invention is drawn to methods for introducing nucleotide constructs into cells from maize plants and for producing stably transformed maize plants. The methods find use in developing new maize cultivars with improved agronomic characteristics. In particular, the methods involve introducing the nucleotide constructs into cells from immature embryos that do not proliferate in culture. Often embryos derived from inbred maize lines, or homozygous maize lines are recalcitrant to the tissue culture process. Provided herein are methods that allow the introduction of the nucleotide construct into cells and regeneration of those cells into stably transformed maize plants. Thus, the methods provide improved methods of transforming cells from immature maize embryos that obviate the need for callus proliferation before the regeneration of a transformed plant.

Transformation of elite maize inbreds is an important technology for developing maize inbreds and hybrids with improved agronomic traits. Work by Armstrong and others (Songstad et al. (1992) Am J Bot 79:761-764) showed that it was possible to interbreed a more culturable, agronomically poor maize line (A188) with an agronomically desirable, less culturable line (B73) to produce a novel line, Hi-II, with increased culturability and regeneration. Hi-II maize has been used for maize transformation for a number of years because of its high transformability and good culturability, but Hi-II is a hybrid. Non-homozygous plants used in developing transgenic traits are problematic. It is easier to determine the effects of a transgene when a uniform, homozygous, background is used. Another disadvantage of using Hi-II in transformation is that it does not have the quality genetics that are present in current elite inbreds. When developing a transgenic product the transgene is moved into an elite background through cross pollination. After the initial cross, backcrossing is used to remove as much of the Hi-II deleterious genome as possible. This is a labor intensive and time consuming process. It would therefore be beneficial to have a transformation protocol that is efficient for elite maize genotypes that do not produce proliferating callus in culture.

A number of terms used herein are defined and clarified in the following section.

An immature maize embryo is a maize embryo that is physiologically less mature than the dormant embryo that would occur in a typical, viable, mature maize kernel.

An isolated embryo is intended an embryo dissected from the maize caryopsis.

A somatic embryo is embryo initiated and developed from vegetative or non-gametic cells.

A micro event is a viable non-proliferating group of cells from single transgenic cell having a somatic immature embryo morphology.

Auxin depleted refers to a culture medium that was prepared without the addition of any auxin or auxin-like growth regulator. A medium that is essentially auxin free or auxin depleted may contain other phytohormones or plant growth regulators.

Phytohormone depleted refers to a culture medium that was prepared without the addition of any phytohormone (also referred to as a plant growth regulator). A medium that is phytohormone depleted is auxin depleted.

An effective amount is an amount of an agent, compound or phytohormone that is capable of causing the desired effect on an organism. It is recognized that an effective amount may vary depending on factors, such as, for example, the organism, the target tissue of the organism, the method of administration, temperature, light, relative humidity and the like. Further, it is recognized that an effective amount of a particular agent may be determined by administering a range of amounts of the agent to an organism and then determining which amount or amounts cause the desired effect.

Pre-cultured embryo(s) are embryo(s) cultured prior to bombardment on a medium which promotes the production of embryogenic tissue and precedes the conditioning of the embryo in preparation for transformation.

Pre-cultured embryos of maize are typically cultured for a period to produce an embryogenic response prior to particle bombardment. The tissue derived from the embryogenic response provides the target cells for transformation. Conditions during this period of pre-bombardment culture generally include a plant growth regulator and a period of time generally from one to seven days or more. The particular conditions depend on the culture medium formulation, genotype, and general health of the donor plant.

Improved methods for obtaining stably transformed maize plants are provided. The methods taught provide an effective process to use immature embryos to obtain transformed maize plants without the need for growing proliferating callus tissue. Particularly, the methods provide means to obtain transformed plants that do not depend on the formation of Type II callus or Type I callus, thus eliminating the need to use maize genotypes that produce callus. This aspect provides an opportunity to use maize genotypes that are known to exhibit slow or poor in vitro embryogenic response.

Methods are provided for transforming immature maize embryos and for producing transgenic maize plants. Such methods find use in the development of improved maize varieties as well as breeding lines which may be used to produce hybrid maize seeds. The methods involve obtaining immature embryos from a maize plant. The methods further involve transforming an embryo. The methods for producing transgenic maize plants additionally involve regenerating such a transformed cell into a stably transformed maize plant.

The methods can involve the use of a transformation medium comprising a high concentration of an osmoticum. The osmoticum can include compounds that are known to be metabolized by plants, and/or compounds that are not known to be metabolized by plants. Osmoticum that are known to be metabolized by plants include but are not limited to osmoticum such as, for example, sucrose, glucose, fructose and maltose, which are routinely used as a carbon source in plant culture media (Vain et al. (1993) Plant Cell Rep 12:84-88) and immature maize embryos (Brettschneider et al. (1997) Theor Appl Genet. 94:737-748, Pareddy et al. (1997) Maydica 42:143-154; Dunder et al. (1995) In: Gene Transfer to Plants (Potrykus and Spangenberg, eds.) Springer-Verlag, NY, pp. 127-138).

A high concentration of an osmoticum is a concentration that is higher than that typically used when the osmoticum is intended solely as a carbon source. The concentration may be any amount over the standard concentration used in the medium, including but not limited to 0.1%, 0.5%, 1%, 5%, 10%, 20%, 50%, 100%, 200%, or 500% or more higher than the standard concentration. The concentration can be denoted in any units including but not limited to weight/volume (w/v), volume/volume (v/v), molarity, molality, or g/liter. For example, sucrose is routinely used at a concentration of about 3% (w/v) as a carbon source in plant culture media. A high concentration of sucrose in a medium is a concentration that exceeds 3% (w/v). For other osmoticum, including those known to be metabolized by plants and those that are not known to be metabolized by plants, a "high concentration" is a concentration that generally exceeds the molar concentration of sucrose in a medium comprising 3% (w/v) sucrose. The osmoticum may be 8%, 12%, 19% or 30% w/v. Optionally, the osmoticum may be 12-19%.

The method encompasses the use of both solid and liquid plant culture media. Those of ordinary skill in the art recognize that the preparation of solid plant culture media typically involves dissolving or suspending the various media components in a solution comprising water. It is recognized that the concentrations of components of such solid media referred herein are the concentrations of the components in the aqueous solution prior to solidification or gelling.

The methods generally employ immature maize embryos. Such embryos are generally isolated from a maize ear that was pollinated less than about 16 days before use, embryos can be pollinated between about 6 and about 16 days before use, embryos are most frequently pollinated between about 9 and about 12 days before use. Generally, such embryos are between about 1.5 mm and 1.8 mm in length measured from the coleoptilar end to the coleorhizal end. Sizing of embryo for explant and transformation is best accomplished by developmental staging rather than by absolute size. Immature embryos are initially translucent. It is when the entire embryo, axis and scutellum, first become opaque, that they reach the proper developmental stage for use in the process. Immature embryos are generally cultured as soon after they become opaque as possible. Size of embryo (length) is roughly correlated with opacity, but both genotype and environment have dramatic altering effects on embryos size.

Such ears may be obtained from any source, including field, greenhouse and/or growth-chamber grown maize plants. Typically, the ear is harvested from the maize plant before isolation of the embryos therein, and is subsequently sterilized or otherwise treated to reduce undesired biological contamination, particularly microbial contamination. Methods are known in the art for reducing or eliminating microbial contamination from live plant tissues, such as maize ears, including, but not limited to, contacting the ear, typically after removal of the husk, with an aqueous solution comprising household laundry bleach.

The methods involve the use of isolated, immature embryos. In one method, the immature embryos are isolated from ears that were harvested in the same 24-hour period as the embryo isolation. However, the methods also encompass the use of ears that are stored for a period of time before embryo isolation. Any method of storing ears may be employed. It is recognized, however, that selected methods of ear storage conditions will substantially preserve the viability of the immature embryos therein. The age of an embryo is determined as the interval of time from pollination of the ear to isolation of the embryo therefrom.

The immature embryos may be obtained from a maize plant by any method known in the art. Typically, the embryos will be isolated from a de-husked ear by excising with a sharp-bladed instrument such as, for example, a scapel, knife or other sharp instrument. Upon isolation from an ear, the immature embryos are typically contacted with transformation medium. However, it is recognized that the immature embryos may be contacted with one or more alternative media before contacting the transformation medium. It is further recognized that such alternative media are media that are not known to promote the formation of embryogenic maize callus and are preferably auxin-depleted or phytohormone-depleted media. Such alternative media may optionally comprise a high concentration of an osmoticum. Further it is recognized that contacting comprises both direct contact of an immature embryo with a medium and indirect contact such as, for example, an immature embryo placed on one side of a filter paper that has its opposite side in contact with the medium.

After contacting an isolated, immature embryo with transformation medium, a nucleotide construct may be introduced into a cell of the embryo immediately thereafter or following a period of time, usually not more than about 24 hours after isolation of the immature embryo.

The type of transformation is not critical to the methods; various methods of transformation are currently available. As newer methods are available to transform host cells they may be directly applied. Accordingly, a wide variety of methods have been developed to insert a DNA sequence into the genome of a host cell to obtain the transcription and/or translation of the sequence. Thus, any method that provides for efficient transformation/transfection may be employed.

Methods for transforming various host cells are disclosed in Klein et al. (1992) Bio/Technol 10:286-291. Techniques for transforming a wide variety of higher plant species are well known and described in the technical, scientific, and patent literature. See, for example, Weising et al. (1988) Ann Rev Genet. 22:421-477.

For example, the DNA construct may be introduced directly into the genomic DNA of the plant cell using techniques such as electroporation, PEG-induced transfection, particle bombardment, silicon fiber delivery, or microinjection. See, e.g., Tomes et al., Direct DNA Transfer into Intact Plant Cells Via Microprojectile Bombardment. pp. 197-213 in Plant Cell, Tissue and Organ Culture, Fundamental Methods. eds. Gamborg and Phillips. Springer-Verlag Berlin Heidelberg N.Y., 1995. The introduction of DNA constructs using polyethylene glycol precipitation is described in Paszkowski et al. (1984) EMBO J. 3:2717-2722. Electroporation techniques are described in Fromm et al. (1985) Proc Natl Acad Sci USA 82:5824. Ballistic transformation techniques are described in Klein et al. (1987) Nature 327:70-73. The methods could also involve microprojectile bombardment to introduce nucleotide constructs into the cells of isolated, immature maize embryos. In particular, microprojectile bombardment may be conducted using a high pressure gas delivery system such as, for example, the invention described in U.S. Pat. No. 5,204,253, for which an embodiment known as Biolistic PDS-1000/He System is available commercially, or using any other device known in the art which is capable of delivering to a cell a nucleotide construct on or in microprojectiles.

If desired, the immature embryo may be oriented on the transformation medium for introduction of the nucleotide construct. For introduction by microprojectile bombardment, the immature embryos may be orientated to optimize entry of the nucleotide-construct-coated microprojectiles into a particular region of the immature embryo. Typically for microprojectile bombardment, the immature embryos are oriented with the scutellum of the immature embryos directly facing the expected path of the nucleotide-construct-coated microprojectiles. It is contemplated that the medium be solid, semisolid or a solid surface floating on top of a liquid or semi-liquid surface (e.g., filter paper on liquid).

Alternatively, the DNA constructs may be combined with suitable T-DNA flanking regions and introduced into a bacterial vector for plant transformation, such as a *Rhizobiaceae* vector, including but not limited to *Agrobacterium rhizogenes* or *Agrobacterium tumefaciens* host vectors. For example, the virulence functions of the *Agrobacterium tumefaciens* host will direct the insertion of the construct and adjacent marker into the plant cell DNA when the cell is infected by the bacteria. *Agrobacterium tumefaciens-meditated* transformation techniques are well described in the scientific literature. See, for example Horsch et al. (1984) Science 233:496-498, and Fraley et al. (1983) Proc Natl Acad Sci USA 80:4803. For instance, *Agrobacterium* transformation of maize is described in U.S. Pat. No. 5,981,840. *Agrobacterium* transformation of monocots is found in U.S. Pat. No. 5,591,616. *Agrobacterium* transformation of soybeans is described in U.S. Pat. No. 5,563,055.

Other methods of transformation include: *Agrobacterium rhizogenes*-induced transformation (see, e.g., Lichtenstein and Fuller In: Genetic Engineering, vol. 6, PWJ Rigby, Ed., London, Academic Press, 1987; and Lichtenstein and Draper, In: DNA Cloning, Vol. II, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16; liposome-induced DNA uptake (see, e.g., Freeman et al. (1984) Plant Cell Physiol 25:1353); and vortexing methods (see, e.g., Kindle (1990) Proc Natl Acad Sci USA 87:1228).

After the introduction of the nucleotide construct, the immature embryos may be transferred to an identification or selection medium, a regeneration medium, or a medium that is for both identification/selection and regeneration. Such media may comprise an auxin, for example 2,4-D. Alternatively, an auxin can be added to a plate containing an auxin-depleted medium. The transfer to another medium or the addition of auxin to the medium may occur immediately following the introduction of the nucleotide construct or, if desired, after a period of time. Typically within about one week or less after the introduction of the nucleotide construct, the immature embryos are transferred from the transformation medium to another medium, or auxin is added to the transformation medium. Usually the embryos are transferred to another medium, or auxin is added to the transformation medium, within about 2 to about 3 days after introduction of the nucleotide construct. Generally, the medium that the immature embryos are transferred to after introduction of the nucleotide construct will depend on the method by which the nucleotide construct was introduced into cells of the immature embryos, the nucleotide construct and the desired outcome. The medium used may additionally comprise other components such as, for example, antibiotics.

Micro events are viable non-proliferating groups of cells having a somatic immature embryo morphology. Micro events are distinct from events which produce Type I or Type II callus. An exemplary comparison of an early Type II event and a micro event is seen in FIG. 1. Both events are from the same ear, which was transformed using *Agrobacterium* containing an YFP expression cassette about 10 weeks prior to the photographs. The early event shows typical Type II callus formation and proliferation, as compared to the micro event which is much smaller (see FIG. 1, Panel A). Panels B and C show the early event using light microscopy, and fluorescence microscopy to identify YFP expressing cells. Panels D and E similarly show images from light microscopy and fluorescence microscopy for the micro event. Micro events are non-proliferating on typical post-delivery callus media. Micro events are essentially latent events until transferred to a maturation media, at which time they proceed to produce plantlets. Since micro events don't proliferate on callus media, they are typically identified over a relatively long time frame after the introduction of the polynucleotide construct of interest. Micro events are characterized by the lack of proliferation as compared to other events produced concurrently. Identification of micro events can be facilitated by the use of a visual marker, including but not limited to a fluorescent marker. For example, micro events can be identified about 3.5-15 weeks after transformation, including but not limited to 3.5, 4, 4.5, 5, 5.5, 6, 6.5, 7, 7.5, 8, 8.5, 9, 10, 11, 12, 13, 14, or 15 weeks after transformation. Micro events can be identified about 23-105 days after transformation, including but not limited to about 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 80, 85, 90, 95, 100, 105, or more days after transformation. Generally, micro events are identifiable at about 8 weeks, or about 56 days, after *Agrobacterium* infection or particle bombardment date.

The transformed cells may be identified or selected and, if desired, regenerated into transformed plants. The methods do not depend on any particular method for identifying or selecting transformed cells from immature embryos and for regenerating such cells into transformed maize plants. Identification methods may involve utilizing a marker gene, such as YFP, CPF, RFP, GFP, or any other fluorescent marker, or a cell cycle gene, such as CKI, or cyclin D. Methods for using GFP and cell cycle genes are found in U.S. Pat. Nos. 6,300,543, 6,518,487, and 7,256,280, herein incorporated by reference. Selection methods typically involve placing the immature embryos, or parts thereof, on a medium that contains a selective agent, promotes regeneration or both. If, for example, the nucleotide construct comprises a selectable marker gene for herbicide resistance that is operably linked to a promoter that drives expression in a plant cell, then selection of the transformed cells may be achieved by adding an effective amount of the herbicide to the medium to inhibit the growth of or kill non-transformed cells. Such selectable marker genes and methods of use are well known in the art. Methods and media employed in the regeneration of transformed maize plants from transformed cells of immature embryos are also known in the art. Generally, such methods comprise contacting the immature embryo with a medium that contains an effective amount of an auxin. Any method known in the art for identifying or selecting transformed plant cells and regenerating transformed maize plants may be employed in the methods.

The methods do not depend on a particular nucleotide construct. Any nucleotide construct that may be introduced into a plant cell may be employed in the methods. Nucleotide constructs comprise at least one nucleotide sequence of interest, optionally the nucleotide sequence of interest is operably linked to a promoter that drives expression in a plant cell. The nucleotide constructs may also comprise identification or selectable marker gene constructs in addition to the nucleotide sequence of interest.

Selectable marker genes may be utilized for the selection of transformed cells or tissues. Selectable marker genes include genes encoding antibiotic resistance, such as nptII which encodes neomycin phosphotransferase II (NEO), hpt which encodes hygromycin phosphotransferase (HPT), and the moncot-optimized cyanamide hydratase gene (moCAH) (see U.S. Pat. No. 6,096,947) as well as genes conferring resistance to herbicidal compounds, such as glufosinate ammonium, bromoxynil, imidazolinones, and 2,4-dichlorophenoxyacetate (2,4-D). See generally, Yarranton (1992) Curr Opin Biotech 3:506-511; Christopherson et al. (1992) Proc Natl Acad Sci USA 89:6314-6318; Yao et al. (1992) Cell 71:63-72; Reznikoff (1992) Mol Microbiol 6:2419-2422; Barkley et al. (1980) in *The Operon*, pp. 177-220; Hu et al. (1987) Cell 48:555-566; Brown et al. (1987) Cell 49:603-612; Figge et al. (1988) Cell 52:713-722; Deuschle et al. (1989) Proc Natl Acad Sci USA 86:5400-5404; Fuerst et al. (1989) Proc. Natl. Acad. Sci. USA 86:2549-2553; Deuschle et al. (1990) Science 248:480-483; Gossen (1993) Ph.D. Thesis, University of Heidelberg; Reines et al. (1993) Proc Natl Acad Sci USA 90:1917-1921; Labow et al. (1990) Mol Cell Biol 10:3343-3356; Zambretti et al. (1992) Proc Natl Acad Sci USA 89:3952-3956; Baim et al. (1991) Proc Natl Acad Sci USA 88:5072-5076; Wyborski et al. (1991) Nucl Acids Res 19:4647-4653; Hillenand-Wissman (1989) Topics Mol Struc Biol.10:143-162; Degenkolb et al. (1991) Antimicrob Agents Chemother 35:1591-1595; Kleinschnidt et al. (1988) Biochemistry 27:1094-1104; Bonin (1993) Ph.D. Thesis, University of Heidelberg; Gossen et al. (1992) Proc Natl Acad Sci USA 89:5547-5551; Oliva et al. (1992) Antimicrob Agents Chemother 36:913-919; Hlavka et al. (1985) *Handbook of Experimental Pharmacology, Vol.* 78 (Springer-Verlag, Berlin); Gill et al. (1988) Nature 334:721-724; all of which are herein incorporated by reference. The above list of selectable marker genes is not meant to be limiting. Any selectable marker gene can be used in the present invention. Other marker genes such as GFP (WO97/41228) may also be utilized.

Likewise, the methods of the invention do not depend on immature maize embryos of a particular genotype. The methods of the present invention may be used with immature maize embryos of any maize genotype including immature embryos from both hybrids and inbreds. Examples of maize genotypes include, but are not limited to, Hi-II and hybrids of a cross between Hi-II and a second genotype such as, for example, PHN46, PHTE4, PHAA0, PHP18, PH05F, PH09B, PHP02, PHJ90, PH24E, PHT05, ASKC27 and PH21T. Examples of elite maize genotypes include but are not limited to PH179P, PH179R, PHP38, PH17P7, PH17T8, PH182Y, PH18F6, PHAPH, PHAC4, PH12K5, PH12SG, PH12SK, PH17T7, PH6PV, PH705, PH7CH, PHAKC, PHAPH, PHCER, PHE0N, PHE4N, PHE67, PHY71, PHEJW, PHEKJ, PHEKN, PHGJ4, PHGMG, PHH4V, PHH5G, PHH7E, PHHC6, PHHEB, PHHJN, PHR1J, PH12P5, PHDTD, PHTMM1, PHW0N, PH6WA, PH726, PHP02, PH51H, PHEDR, PHEWB, PH581, PH8JR, PHAJE, PHCJP, PHR03, PHHHN, PHN46, PH1CA, PH4CN, and PHH9H. Elite inbreds are typically inbred maize genotypes that are used to produce commercial hybrid maize lines.

The methods involve producing a stably transformed maize plant. Such a transformed maize plant is a fertile maize plant that is capable of producing at least one transformed progeny. The methods provide a way to identifying viable immature embryos comprising a transformed maize cell having the polynucleotide of interest. The methods further provide means to produce more transformed maize plants from a transformation experiment as compared to a control method that does not identify or transfer a micro event to a regeneration media to produce a transformed maize plant comprising the polynucleotide of interest. In some examples, the methods provide at least 10% to greater than 100% more transformed maize plants as compared to a control method that does not identify the micro events. In some examples, the methods provide at least 10%, 15%, 20%, 25%, 30%, 35%, 40%, 45%, 50%, 55%, 60%, 65%, 70%, 75%, 80%, 85%, 90%, 95%, or 100% more transformed maize plants as compared to a control method.

The methods involve the use of plant culture media. Any plant culture medium known in the art may be employed in the methods including, but not limited to, a transformation support medium, identification or selection medium and a regeneration medium. Typically, such media comprise water, a basal salt mixture and a carbon source, and may additionally comprise one or more other components known in the art, including but not limited to, vitamins, co-factors, myo-inositol, selection agents, charcoal, amino acids, silver nitrate and phytohormones. If a solid plant culture medium is desired, then the medium additionally comprises a gelling agent such as, for example, gelrite, agar or agarose.

For example, transformation medium 560Y comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I H$_2$0 following adjustment to pH 5.8 with KOH); 2.0 g/l Gelrite (added after bringing to volume with D-I H$_2$O); and 8.5 mg/l silver nitrate (added after sterilizing the medium and cooling to room temperature). Selection medium 560R comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I H$_2$0 following adjustment to pH 5.8 with KOH); 3.0 g/l Gelrite (added after bringing to volume with D-I H$_2$O); and 0.85 mg/l silver nitrate and 3.0 mg/l bialaphos (both added after sterilizing the medium and cooling to room temperature).

Plant regeneration medium 288J comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I H$_2$0) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I H$_2$0 after adjusting to pH 5.6); 3.0 g/l Gelrite (added after bringing to volume with D-I H$_2$O); and 1.0 mg/l indoleacetic acid and 3.0 mg/l bialaphos (added after sterilizing the medium and cooling to 60° C.). Phytohormone-depleted medium 272V comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H$_2$O), 0.1 g/l myo-inositol, and 40.0 g/l sucrose (brought to volume with polished D-I H$_2$0 after adjusting pH to 5.6); and 6 g/l bacto-agar (added after bringing to volume with polished D-I H$_2$O), sterilized and cooled to 60° C.

The methods optionally use phytohormones and/or plant growth regulators such as, for example, auxins, cytokinins, gibberellins and ethylene. The phytohormones may include, but are not limited to, both free and conjugated forms of naturally occurring phytohormones or plant growth regulators. Additionally, the phytohormones encompass synthetic analogues and precursors of such naturally occurring phytohormones and synthetic plant growth regulators. Naturally occurring and synthetic analogues of auxins and auxin-like growth regulators include, but are not limited to, indoleacetic acid (IAA), 3-indolebutyric acid (IBA), α-napthaleneacetic acid (NAA), 2,4-dichlorophenoxyacetic acid (2,4-D), 4-(2,4-dichlorophenoxy) butyric acid, 2,4,5-trichlorophenoxyacetic acid (2,4,5-T), 3-amino-2,5-dichlorobenzoic acid (chloramben), (4-chloro-2-methylphenoxy)acetic acid (MCPA), 4-(4-chloro-2-methylphenoxy) butanoic acid (MCPB), mecoprop, dicloprop, quinclorac, picloram, triclopyr, clopyralid, fluoroxypyr, dicamba and combinations thereof. It is recognized that such combinations can be comprised of any possible combination of two or more molecules selected from the group consisting of naturally occurring auxins, synthetic analogues of auxins, and auxin-like growth regulators. By "auxin-like growth regulator" is intended a compound that is not considered an auxin but possesses at least one biological activity that is the substantially the same as that of a naturally occurring auxin.

Examples of phytohormones include naturally occurring compounds, synthetic analogues of cytokinins, and cytokinin-like growth regulators including, but not limited to kinetin, zeatin, zeatin riboside, zeatin riboside phosphate, dihydrozeatin, isopentyl adenine 6-benzyladenine and combinations thereof. It is recognized that such combinations can be comprised of any possible combination of two or more molecules selected from the group consisting naturally occurring cytokinins, synthetic analogues of cytokinins and cytokinin-like growth regulators. By "cytokinin-like growth regulator" is intended a compound that is not considered a cytokinin but possesses at least one biological activity that is the substantially the same as that of a naturally occurring cytokinin.

A nucleotide construct includes any polynucleotide molecule that has been isolated and/or modified as compared to its native source, it is not limited to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs encompass all nucleotide constructs which can be employed in the methods for transforming maize plants including, but not limited to, those comprised of deoxyribonucleotides, ribonucleotides and combinations thereof. Such deoxyribonucleotides and ribonucleotides include both naturally occurring molecules and synthetic analogues. The nucleotide constructs also encompass all forms of nucleotide constructs including, but not limited to, single-stranded forms, double-stranded forms, hairpins, stem-and-loop structures and the like.

Furthermore, it is recognized that the methods may employ a nucleotide construct that is capable of directing, in a transformed plant, the expression of at least one protein, or at least one RNA, such as, for example, an rRNA, a tRNA and an antisense RNA that is complementary to at least a portion of an mRNA. Typically such a nucleotide construct is comprised of a coding sequence for a protein or an RNA operably linked to 5' and 3' transcriptional regulatory regions. Alternatively, it is also recognized that the methods may employ a nucleotide construct that is not capable of directing, in a transformed plant, the expression of a protein or an RNA.

In addition, it is recognized that methods do not depend on the incorporation of the entire nucleotide construct into the genome, only that the genome of the maize plant is altered as a result of the introduction of the nucleotide construct into a maize cell. Alterations to the genome include additions, deletions and substitution of nucleotides in the genome. While the methods do not depend on additions, deletions, or substitutions of any particular number of nucleotides, it is recognized that such additions, deletions or substitutions comprise at least one nucleotide.

The nucleotide constructs also encompass nucleotide constructs, that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides and recombinogenic oligonucleobases.

The nucleotide constructs may be comprise at least one expression cassette for expression in the maize plant of interest. The expression cassette can include 5' and 3' regulatory sequences operably linked to a gene of interest sequence of the invention. Operably linked indicates a functional linkage between two nucleotide sequences, for example a functional linkage of a promoter and a second sequence, such that the promoter sequence initiates and mediates transcription of the DNA sequence corresponding to the second sequence. In some examples, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

An expression cassette may be provided with a plurality of restriction sites for insertion of the gene of interest sequence to be under the transcriptional regulation of the regulatory regions. The expression cassette may additionally contain identification or selectable marker genes.

The expression cassette may include in the 5'-3' direction of transcription, a transcriptional and translational initiation region, a gene of interest sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. A "foreign" sequence is one that is not naturally found in the host plant, for example a foreign transcriptional initiation region is not found in the native plant into which the transcriptional initiation region is introduced. As used herein, a chimeric gene comprises a coding sequence operably linked to a transcription initiation region that is heterologous to the coding sequence.

In other examples, constructs which express the gene of interest using native promoter sequences may be used. Such constructs typically change expression levels of the gene of the interest in the plant or plant cell. Thus, it is expected that the phenotype of the plant or plant cell is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) Mol Gen Genet. 262:141-144; Proudfoot (1991) Cell 64:671-674; Sanfacon et al. (1991) Genes Dev 5:141-149; Mogen et al. (1990) Plant Cell 2:1261-1272; Munroe et al. (1990) Gene 91:151-158; Ballas et al. (1989) Nucl Acids Res 17:7891-7903; and Joshi et al. (1987) Nucl Acid Res 15:9627-9639.

Where appropriate, the nucleotide sequence of interest, such as a gene(s) may be optimized for increased expression in the transformed plant. That is, the genes can be synthesized using plant-preferred codons for improved expression. See, for example, Campbell and Gowri (1990) Plant Physiol 92:1-11 for a discussion of host-preferred codon usage. Methods are available in the art for synthesizing plant-preferred genes. See, for example, U.S. Pat. Nos. 5,380,831, and 5,436,391 and Murray et al (1989) Nucl Acids Res 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5'-leader sequences in the expression cassette construct. Such leader sequences can act to enhance translation. Translation leaders are known in the art and include: picornavirus leaders, for example, EMCV leader (Encephalomyocarditis 5'-noncoding region) (Elroy-Stein et al. (1989) Proc Natl Acad Sci USA 86:6126-6130); potyvirus leaders, for example, TEV leader (Tobacco Etch Virus) (Allison et al. (1986); MDMV leader (Maize Dwarf Mosaic Virus); Virology 154:9-20), and human immunoglobulin heavy-chain binding protein (BiP), (Macejak et al. (1991) Nature 353:90-94); untranslated leader from the coat protein mRNA of alfalfa mosaic virus (AMV RNA 4) (Jobling et al. (1987) Nature 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) Virology 81:382-385). See also, Della-Cioppa et al. (1987) Plant Physiol 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, recombination sites, removal of superfluous DNA, removal of restriction sites, operable linkages, fusions, or the like. For this purpose, in vitro mutagenesis, primer repair, restriction, annealing, resubstitutions, e.g., transitions and transversions, may be involved.

Any promoter can be used, and is typically selected based on the desired outcome. A promoter is a region of DNA involved in recognition and binding of RNA polymerase and other proteins to initiate transcription. A plant promoter is a promoter capable of initiating transcription in a plant cell, for a review of plant promoters see Potenza et al. (2004) In Vitro Cell Dev Biol 40:1-22. The nucleic acids can be combined with constitutive, tissue-preferred, developmental, inducible, or other promoters for expression in maize plants.

Depending on the desired result, it may be beneficial to express a gene under the control of an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) Neth J Plant Pathol 89:245-254; Uknes et al. (1992) Plant Cell 4:645-656; and Van Loon (1985) Plant Mol. Virol. 4:111-116. See also WO99/43819, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoidinducible promoter in Schena et al. (1991) Proc Natl Acad Sci USA 88:10421-10425 and McNellis et al. (1998) Plant J 14:247-257) and tetracycline-inducible and tetracycline-repressible promoters (see, for example, Gatz et al. (1991) Mol Gen Genet. 227:229-237, and U.S. Pat. Nos. 5,814,618 and 5,789,156), herein incorporated by reference.

Various changes in phenotype are of interest including modifying the fatty acid composition in a plant, altering the amino acid content of a plant, altering a pathogen defense mechanism, modifying stress response, modifying yield, modifying nutrient needs and/or utilization, modifying plant architecture, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes or nucleotide sequences of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increases, the choice of genes for transformation will change accordingly. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Grain traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,737,514; 5,723,756; 5,593,881; and Geiser et al. (1986) Gene 48:109); lectins (Van Damme et al. (1994) Plant Mol Biol 24:825); and the like.

Genes encoding disease resistance traits include detoxification genes, such as against fumonosin (see, e.g., U.S. Pat. Nos. 5,716,820, 5,792,931, 6,025,188, 6,229,071, and 6,573,075); avirulence (avr) and disease resistance (R) genes (Jones et al. (1994) Science 266:789; Martin et al. (1993) Science 262:1432; and Mindrinos et al. (1994) Cell 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical emasculation. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of seed is reflected in traits such as levels and types of oils, saturated and unsaturated, quality and quantity of essential amino acids, and levels of cellulose. For example, U.S. Pat. Nos. 5,990,389; 5,885,801; and 5,885,802 and U.S. Pat. No. 5,703,409, provide descriptions of modifications of proteins for desired purposes.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321.

Exogenous products include plant enzymes and products as well as those from other sources including prokaryotes and other eukaryotes. Such products include enzymes, cofactors, hormones, and the like. The level of proteins, particularly modified proteins having improved amino acid distribution to improve the nutrient value of the plant, can be increased.

Putative events, regenerated plants, and/or progeny thereof are usually subjected to various analyses to develop a molecular characterization of the event. Analyses include but are not limited to methods and tools that verify that the expression cassette(s) were transferred intact with no partial deletions, duplications, or rearrangement of elements, that detect the presence or absence of vector backbone, that measure the copy number of the transgene(s) of interest, and the like. Typically, events having a single copy of the transgene(s) of interest are selected for further analysis and/or advancement. Transformation experiments vary in the frequency of single copy events. For example, the frequency of single copy events can range from 10%-100% of the events, including but not limited to about 10%, 15%, 20%, 25%, 30%, 40%, 45%, 50%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 90%, 95%, or 100% of the total number of events generated.

The following examples are presented by way of illustration, not by way of limitation.

EXAMPLES

Any transformation method and standard media can be used. The following is an exemplary set of media and protocols.

TABLE 1

Composition of media used:

| Media | Composition (Unit Volume = 1 L) |
|---|---|
| 561Q | 4.0 g Chu(N6) basal salts, 1 ml Eriksson's vitamins 1000X, 0.5 mg thiamine HCl, 1.5 mg 2,4-D, 0.69 g L-proline, 68.5 g sucrose, 36 g glucose, pH 5.2 |
| 562P | 4.0 g Chu(N6) basal salts, 1 ml Eriksson's vitamins 1000X, 0.5 mg thiamine HCl, 2.0 mg 2,4-D, 0.69 g L-proline, 30 g sucrose, 0.85 mg silver nitrate, 1 ml acetosyringone @ 100 mM, 3.0 g Gelrite, pH 5.8 |
| 563O | 4.0 g Chu(N6) basal salts, 1 ml Eriksson's vitamins 1000X, 0.5 mg thiamine HCl, 1.5 mg 2,4-D, 0.69 g L-proline, 30 g sucrose, 0.5 g MES buffer, 0.85 mg silver nitrate, 3 mg Bialaphos, 100 mg carbenicillin, 8.0 g agar, pH 5.8 |
| 289B | 4.3 g MS basal salt mixture, 1 g myo-inositol, 0.5 mg |

TABLE 1-continued

Composition of media used:

| Media | Composition (Unit Volume = 1 L) |
|---|---|
|  | nicotinic acid, 0.1 mg thiamine.HCl, 0.5 mg pyridoxine.HCl, 2 mg glycine, 0.5 mg zeatin, 1 mg IAA @ 0.5 mg/ml, 1 ml ABA @ 0.1 mM, 1.5 mg Bialophos, 100 mg carbenicillin, 60.0 g sucrose, 3.0 g Gelrite, pH 5.6. |
| 271C | 4.3 g MS basal salt mixture, 0.1 g myo-inositol, 0.5 mg nicotinic acid, 0.1 mg thiamine HCl, 0.5 mg pyridoxine HCl, 2 mg glycine, 40 g sucrose, 3 mg Bialophos, 1.5 g Gelrite, pH 5.6. |
| 272 | 4.3 g MS basal salt mixture, 0.1 g myo-inositol, 0.5 mg nicotinic acid, 1 mg thiamine HCl, 0.5 mg pyridoxine.HCl, 2 mg glycine, 40 g sucrose, 1.5 g Gelrite, pH 5.6. |
| 800 | 3 g potassium phosphate dibasic, 1 g sodium phosphate monobasic anhydrous, 1 g ammonium chloride, 0.3 g magnesium sulfate heptahydrate, 0.15 g potassium chloride, 100 mg calcium chloride anhydrate, 25 mg ferrous sulfate heptahydrate, 9 g agar, 5 g glucose, 100 mg spectinomycin, pH 7.0 |
| 810D | 5 g yeast extract, 10 g Peptone, 5 g sodium chloride, 15 g agar, 50 mg spectinomycin, pH 6.8. |
| 12S | 5 g glucose, 15 g agar, 2.5 mg ferrous sulfate heptahydrate, 3 g potassium phosphate dibasic, 1 g sodium phosphate monobasic anhydrous, 1 g ammonium chloride, 0.3 g magnesium sulfate heptahydrate, 0.15 g potassium chloride, 14.4 mg calcium chloride anhydrate, 50 mg spectinomycin. |

*Agrobacterium* Transformation of Hi-II Maize

Isolation of Fresh Embryos

1 Ears are harvested when the embryo size reaches 1.0-2.0 mm. The ear sources are greenhouse, field or growth chamber.

2 Ears are sterilized with a 20%-30% bleach solution made with diH$_2$O adding 2-4 drops of a surfactant, for 20 minutes (no longer than 30 minutes). Drain the solution from each container and rinse the ears three times with sterile diH$_2$O 3 Add 2 ml of 561Q medium into a sterile 2 ml microcentrifuge tube for embryo isolation. Label the tops and sides of the microcentrifuge tubes as needed.

4 Dissect embryos from the ear and drop the embryos into the microcentrifuge tube(s) containing 561Q media.

Preparation of *Agrobacterium* Suspension for Agroinfection

5 *Agrobacterium* master plate: Pick up frozen *Agrobacterium* (−80° C.) and streak on 800 or 12S medium and culture at 28° C. in dark for 2-3 days. This plate can be stored at 4° C. and used usually for 1 month.

6 Pick up a colony from the master plate and streak on an 810D medium plate (containing 50 mg/L spectinomycin) and incubate in the dark at 28° C. for 1-2 days.

7 Collect the *Agrobacterium* growth from this plate with a loop and suspend it into a 14 ml Falcon tube with 561Q medium and shake by hand to reach an even suspension.

8 Take 1 ml of the solution and dispense into a disposable spectrophotometer cuvette, use 561Q as blank control to measure the OD. Adjust the suspension to give an OD of 0.35-0.45 at 550 nm under visible light. *Agrobacterium* concentration is 1×10$^9$ cfu/ml at an OD of 0.72.

*Agrobacterium* Infection of Embryos, Co-culture

9 Remove the medium from the tube containing the fresh embryos.

10 Add 1 ml of the *Agrobacterium* suspension at OD described above and vortex at low speed for 15-30 second.

11 Stand the tube for 5 minutes at room temperature in the hood.

12 Pour the suspension with embryos onto 562P plate. Transfer any embryos that are left in the tube or cap onto the plate with a sterile spatula. Check that the plate is labeled to include: *Agrobacterium* ID (optionally: ear source, ear genotype, ear number, pollination and harvest dates).

13 Remove the extra *Agrobacterium* with a pipette, and place the embryos axis down on the medium. All of the embryos from a single ear are placed on one 562P plate. Seal the plate with Parafilm™.

14 Incubate the plate in the dark for 3 days at 21° C.

15 Transfer the plate in dark for 4-7 days at 26° C.

Selection and Regeneration

16 Transfer all of the embryos from 562P to 563O plates. Spread out about 20 embryos per plate. Seal the plate(s) with Parafilm™ (optional). Incubate the plates in the dark at 26° C.

17 After two weeks, subculture the embryos onto 563O and continue incubation under the same conditions. Seal the plate with Parafilm™ (optional).

18 After three weeks, pick up the events based on one event per embryo. Place one event onto a single 563O plate (denoted as early event). If less than 12 events picked or if events appear to be of poor quality, transfer the rest of the embryos to fresh 563O plate.

19 After two weeks, examine the plates for more events as needed (denoted as late event). Transfer the both early and later apparent embryogenic events to 289B medium as a small amount in a one spot. Transfer all the rest of embryos to 289B medium as 20 embryos or less per plate for micro event development if less than 12 events picked or events appear to have poor quality. Incubate all events in 289B in the dark for two weeks at 26° C. for the conversion of immature somatic embryos into matured somatic embryos. Record early and later event numbers, and total embryos number in common frequency sheet.

20 After two weeks, the material that has visible shoots and roots is transferred onto 271C or 272 medium and is placed under artificial light at 26° C.

21 One week later the plantlets are placed into tubes containing 272 medium. Generally progress two plantlets per event.

22 Choose the healthiest, most vigorous plant per event (e.g., 10 plants from 10 events) and send them to a greenhouse.

Agrobacterium Transformation of Hi-II

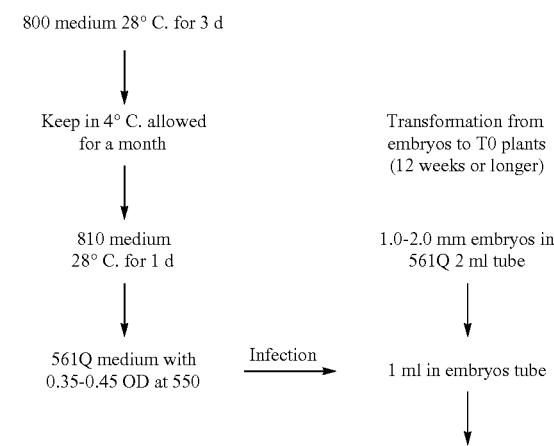

-continued

Co-cultivation in 562P at 21° C. for 3 d

↓

Co-cultivation in 562P at 26° C. for 4-6 d

↓

Selection in 563O for 2 week

↓

Selection in 563O for 3 week

↓

Pick up early event to 563O for 2 week

↓

Pick up later event & somatic embryo maturation in 289B 2 week

↓

Identify micro-event & germination for all events

↓

Plantlet growth in 272 tubes 1 week, sent to greenhouse

TABLE 1

Number & Frequency of Events with Different Transgene Copy Number

| Event Type | 1 copy | | 2 copies | | 3 copies | | >3 copies | |
|---|---|---|---|---|---|---|---|---|
| Early Event | 396 | 58% | 150 | 22% | 66 | 10% | 73 | 10% |
| Late Event | 52 | 56% | 17 | 18% | 18 | 19% | 6 | 7% |
| Micro Event | 27 | 71% | 5 | 13% | 3 | 8% | 3 | 8% |

A method is described for increasing the number of events generated from a plant DNA transformation experiment. After transformation and transfer of embryos to selection media, regular events will appear in an predetermined and expected period of time. The remaining embryos fail to produce any detectable callus growth within this window of time and are usually discarded. We found that some of those embryos are still event competent. Once transferred to regeneration media, those embryos will develop to mature transgenic embryos, which can be regenerated into transgenic plants in the same manner as regular events. Micro events are quiescent, non-proliferating or slow-proliferating groups of transgenic cells that can only be seen under the microscope. Micro events are normal and functional transgenic events, i.e. they do regenerate into normal plants just like any other event. Table 1 summarizes the copy number frequency and event type for a transformation experiment. This analysis showed an apparent tendency to contain single copy inserts as compared to other regular events (early and late). Statistical analysis of this data did not confirm this apparent tendency. A Cochran-Armitage test with permutation resampling indicated no significant difference among the three types of events in their copy number distribution (P<0.01). Using chi-squared analysis of micro event vs. early event or late event with 3 degrees of freedom, $\chi^2=4.542$, two-tailed P-value=0.2085, which is not statistically significant.

Typically, non-proliferating callus would be considered negative and discarded early in the process. These events are not identifiable to the naked eye, they were identified by microscopic examination of transformed embryos. All events were maintained and typed as early, late, or micro event for 36 constructs. Events appearing 6 weeks post-*Agrobacterium* infection were denoted as early events, those appearing 8 weeks post-*Agrobacterium* infection were denoted as late events. The data are summarized in Table 2.

TABLE 2

| Construct | Early | Late | Total | Micro 1 wk 271C | 2 wks 271C | 3 wks 271C | Total |
|---|---|---|---|---|---|---|---|
| AP0004.A07 | 0 | 0 | 0 | 0 | 0 | 0 | 0 |
| AP0004.B07 | 3 | 0 | 3 | 0 | 0 | 0 | 0 |
| AP0004.C07 | 2 | 1 | 3 | 4 | 0 | 2 | 6 |
| AP0004.D07 | 0 | 0 | 0 | 0 | 0 | 0 | 0 |
| AP0004.E07 | 1 | 2 | 3 | 0 | 0 | 0 | 0 |
| AP0004.F07 | 0 | 0 | 0 | 5 | 1 | 0 | 6 |
| AP0004.G07 | 2 | 3 | 5 | 4 | 1 | 0 | 5 |
| AP0004.H07 | 3 | 0 | 3 | 4 | 0 | 0 | 4 |
| AP0004.A08 | 4 | 8 | 12 | 0 | 0 | 0 | 0 |
| AP0004.B08 | 1 | 0 | 1 | 2 | 4 | 1 | 7 |
| AP0004.C08 | 2 | 5 | 7 | 8 | 2 | 2 | 12 |
| AP0004.D08 | 1 | 0 | 1 | 4 | 1 | 0 | 5 |
| AP0004.E08 | 0 | 0 | 0 | 0 | 1 | 1 | 2 |
| AP0004.F08 | 2 | 0 | 2 | 1 | 0 | 2 | 3 |
| AP0004.G08 | 2 | 0 | 2 | 0 | 0 | 0 | 0 |
| AP0004.H08 | 3 | 1 | 4 | 1 | 0 | 1 | 1 |
| AP0004.A09 | 1 | 2 | 3 | 0 | 1 | 0 | 1 |
| AP0004.B09 | 1 | 1 | 2 | 0 | 0 | 0 | 0 |
| AP0004.C09 | 1 | 1 | 2 | 0 | 0 | 0 | 0 |
| AP0004.D09 | 0 | 0 | 0 | 3 | 0 | 1 | 4 |
| AP0004.E09 | 4 | 2 | 6 | 1 | 0 | 0 | 1 |
| AP0004.F09 | 0 | 1 | 1 | 1 | 0 | 0 | 1 |
| AP0004.G09 | 2 | 1 | 3 | 2 | 1 | 0 | 3 |
| AP0004.H09 | 1 | 3 | 4 | 1 | 4 | 0 | 5 |
| AP0004.A10 | 3 | 0 | 3 | 1 | 0 | 0 | 1 |
| AP0004.B10 | 0 | 0 | 0 | 1 | 0 | 0 | 1 |
| AP0004.C10 | 1 | 0 | 1 | 0 | 0 | 0 | 0 |
| AP0004.D10 | 1 | 1 | 2 | 0 | 0 | 0 | 0 |
| AP0004.E10 | 1 | 0 | 1 | 3 | 1 | 0 | 4 |
| AP0004.F10 | 1 | 0 | 1 | 0 | 1 | 0 | 1 |
| AP0004.G10 | 4 | 1 | 5 | 3 | 0 | 0 | 3 |
| AP0004.H10 | 6 | 5 | 11 | 5 | 0 | 0 | 5 |
| AP0004.A11 | 7 | 1 | 8 | 4 | 0 | 0 | 4 |
| AP0004.B11 | 3 | 4 | 7 | 10 | 0 | 0 | 10 |
| AP0004.C11 | 0 | 3 | 3 | 5 | 0 | 0 | 5 |
| AP0004.D11 | 12 | 4 | 16 | 0 | 0 | 0 | 0 |
| Totals | 75 | 50 | 125 | 73 | 18 | 9 | 100 |

As seen in Table 2, the ability to identify additional events can significantly increase the number of usable events produced from each transformation experiment. Identification of micro events can contribute an increase of ≧80% in the number of usable events. This contribution could be especially important in efficiency limiting processes such as high throughput transformation methods, transformation of elite or recalcitrant lines, etc.).

That which is claimed:

1. A method for producing a transformed maize plant, said method comprising:
   (a) isolating an immature embryo from a maize ear;

(b) introducing a polynucleotide of interest into at least one cell of said immature embryo to produce a transformed maize cell;

(c) culturing said immature embryo having a transformed cell on a callus selection media comprising an effective amount of an auxin for a time period and conditions sufficient for early and late callus formation events to occur;

(d) identifying at least one early or late event from the culture of step (c);

(e) identifying a micro event from the culture of step (c) wherein the micro event is a viable non-proliferating group of cells from a single transgenic cell compared to early and late events in steps (c) to (d) and the micro event having a somatic immature embryo morphology; and (f) regenerating a transformed maize plant from the micro event of step (e).

wherein the transformed maize plant comprises the polynucleotide of interest.

2. The method of claim 1, wherein said auxin is 2,4-D.

3. The method of claim 1, wherein said auxin is 2-methoxy-3,6-dichlorobenzoic acid.

4. The method of claim 1, wherein the selection media of (c) further comprises a cytokinin.

5. The method of claim 4, wherein said cytokinin is 6-benzylaminopurine (BAP).

6. The method of claim 4, wherein said cytokinin is 1-phenyl-3-(1,2,3-thiadiazol-5-yl)urea.

7. The method of claim 4, wherein said cytokinin is a zeatin.

8. The method of claim 1, wherein at least 40% of the transformed maize plants produced by the method have a single copy of the polynucleotide of interest.

9. The method of claim 1, wherein the polynucleotide of interest is introduced using *Agrobacterium*.

10. The method of claim 1, wherein the polynucleotide of interest is introduced using particle bombardment.

11. The method of claim 1, wherein in step (e) said micro event is identified after at least 8 weeks in culture.

12. The method of claim 1, wherein in step (c) said culture conditions comprise culturing in the dark and culturing at greater than about 21° C.

\* \* \* \* \*